United States Patent
Duncan et al.

(10) Patent No.: US 10,188,405 B2
(45) Date of Patent: Jan. 29, 2019

(54) DEVICE FOR USE IN ORTHOPAEDIC SURGERY

(71) Applicant: DEPUY IRELAND UNLIMITED COMPANY, County Cork (IE)

(72) Inventors: Luke Duncan, Newbury (GB); Jason Naylor, Leeds (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 335 days.

(21) Appl. No.: 15/025,970

(22) PCT Filed: Sep. 30, 2014

(86) PCT No.: PCT/EP2014/070903
§ 371 (c)(1),
(2) Date: Mar. 30, 2016

(87) PCT Pub. No.: WO2015/049223
PCT Pub. Date: Apr. 9, 2015

(65) Prior Publication Data
US 2016/0235417 A1    Aug. 18, 2016

(30) Foreign Application Priority Data
Oct. 1, 2013 (GB) .................................. 1317331.5

(51) Int. Cl.
*A61B 17/16*    (2006.01)
*A61B 17/00*    (2006.01)

(52) U.S. Cl.
CPC ...... *A61B 17/1668* (2013.01); *A61B 17/1659* (2013.01); *A61B 2017/00526* (2013.01)

(58) Field of Classification Search
CPC .................................................. A61B 17/1668
See application file for complete search history.

(56) References Cited

U.S. PATENT DOCUMENTS

| | | | | |
|---|---|---|---|---|
| 5,006,121 A * | 4/1991 | Hafeli | ............... | A61B 17/1659 606/79 |
| 5,124,106 A * | 6/1992 | Morr | .................. | A61B 17/1659 264/221 |
| 5,124,186 A | 6/1992 | Wycech | | |
| 5,454,815 A * | 10/1995 | Geisser | ............. | A61B 17/1659 606/79 |

(Continued)

FOREIGN PATENT DOCUMENTS

| | | |
|---|---|---|
| EP | 1611854 A1 | 1/2006 |
| EP | 2208469 A1 | 7/2010 |

*Primary Examiner* — Zade Coley

(57) ABSTRACT

A device (10) for use in orthopedic surgery includes a metallic central member (30). The device also includes an outer portion (20) comprising a polymer, which can be molded around the metallic central member. The outer portion thus surrounds the metallic central member. The outer portion has a profiled outer surface (40), such as teeth, ribs or ridges for removing bone. Engagement features for resisting relative movement between the metallic central member and the outer portion can comprise ridges, grooves (34, 36) and apertures (32) of the metallic central member, filled with polymer. The device can be a broach or rasp. A surgical instrument kit includes a plurality of differently sized devices of the kind described herein.

10 Claims, 2 Drawing Sheets

(56) References Cited

U.S. PATENT DOCUMENTS

| | | | | |
|---|---|---|---|---|
| 8,679,127 B2* | 3/2014 | Biegun | ............... | A61B 17/154 606/87 |
| 8,702,807 B2* | 4/2014 | Hood | ................... | A61F 2/4657 623/22.42 |
| 2006/0111725 A1* | 5/2006 | Biegun | ............... | A61B 17/154 606/85 |
| 2008/0215159 A1 | 9/2008 | Stamp | | |
| 2013/0200550 A1* | 8/2013 | Biegun | ............ | B29C 45/14631 264/279.1 |

* cited by examiner

DEVICE FOR USE IN ORTHOPAEDIC SURGERY

CROSS REFERENCE TO RELATED PCT APPLICATION

This application is a National Stage 35 U.S.C. 371 of International Patent Application PCT/EP2014/070903 filed Sep. 30, 2014, which claims priority to United Kingdom Application No. 1317331.5, filed Oct. 1, 2013, both of which are incorporated by reference in their entireties.

FIELD OF THE INVENTION

This invention relates to a device for use in orthopaedic surgery. This invention also relates to a kit including a plurality of the devices. This invention further relates to a method of removing bone during orthopaedic surgery.

BACKGROUND OF THE INVENTION

Orthopaedic surgery often involves the installation of an implant. One example of such a procedure is the installation of a femoral implant in which the femoral head is replaced with a metallic implant having a ball and a stem that extends into the medullary canal of the femur for securing the implant. This procedure involves cutting through the femoral neck to remove the head and to obtain access to the medullary canal. After the cut through the femoral neck has been made, a broach or rasp is used to remove bone that has been exposed by the cut, in order to clear an opening to the medullary canal and to prepare the medullary canal itself so that the femoral implant can be installed.

Normally, the broach or rasp that is used to remove the bone comprises an elongate metallic body having a tip at one end and an outer surface that includes features such as ridges or teeth. The ridges or teeth can be engaged with the bone to be removed while the broach or rasp is moved back and forth, thereby to scrape the bone away. The tip of the device can be used as a pick, to chip bone away. These kinds of metallic broach or rasp comprise a monolithic metallic body. A disadvantage associated with broaches or rasps of this kind is that they are expensive to manufacture. Another disadvantage is that they are typically very heavy, which can make them difficult for a surgeon to manipulate effectively during a surgical procedure. On the other hand, the fact that the broach or rasp comprises a solid metal body does mean that the broach or rasp is particularly rigid.

In order to reduce the weight and cost associated with the metallic broaches and rasps described above, it has been proposed to manufacture devices using alternative materials. In particular, it has been proposed that instead of metal, a polymer may be used. One example of this is described in U.S. Pat. No. 5,454,815, which describes a bone rasp having a plastic toothed working section with teeth and cutting edges. The rasp is intended to be manufactured inexpensively, making it suitable for one-time use and thereby making cleaning and sterilisation of the used rasp unnecessary. The rasp includes a connecting section for connecting the rasp to an impact tool. Other devices comprised entirely of a polymer have also elsewhere been proposed.

A problem with the non-metallic device described above is that it does not have the same rigidity as the earlier metallic devices. During a surgical procedure involving the removal of bone, a broach or rasp is subjected to a significant amount of stress as it is impacted against the bone. Plastic broaches or rasps are less suited for withstanding these forces and may potentially break or fracture during the procedure. Surgeons are also known to prefer using metallic broaches because they are rigid and do not yield when pressed against the bone to be removed.

Accordingly, there is a need for an alternative approach to reducing the cost and weight of medical devices such as broaches or rasps, in which at least some of the sturdiness and rigidity of earlier solid metal devices may be retained.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a device for use in orthopaedic surgery. The device includes a metallic central member. The device also includes an outer portion comprising a polymer. The outer portion surrounds the metallic central member. The outer portion has a profiled outer surface for removing bone.

A device such as a broach or rasp having a metallic central member surrounded by an outer portion comprising a polymer is relatively light compared to earlier devices comprised of solid metal. The device is also stronger and more rigid than earlier devices formed entirely from a polymer. Accordingly, the device can more durable than known devices and can better withstand impaction forces involved in bone removal, for example during when preparing the medullary cavity of a patient to receive an implant.

According to another aspect of the invention, there is provided a surgical instrument kit comprising a plurality of differently sized devices of the kind described above.

The provision of a kit including differently sized devices, such as broaches or rasps, of the kind described here can conveniently allow a surgeon to select one or more appropriately sized devices for use in a surgical procedure.

According to a further aspect of the invention, there is provided a method of removing bone during orthopaedic surgery. The method includes providing a device comprising a metallic central member and an outer portion comprising a polymer, wherein the outer portion surrounds the metallic central member and has a profiled outer surface. The method also includes impacting the device to remove the bone using the profiled outer surface.

Although devices made entirely of polymer are lighter and cheaper to manufacture, surgeons typically prefer devices such as broaches or rasps that have the rigidity of solid metal. Embodiments of this invention can provide a device that is both light and rigid.

The metallic central member can include one or more engagement features for resisting movement of the metallic central member relative to the outer portion during impaction of the device. The engagement features thus add to the structural stability of the device. The engagement features can take a number of forms. For example, at least some of them can include an aperture that passes through the metallic central member and which can be filled with the polymer of the outer portion. At least some of the engagement features can be ridges or grooves on an outer surface of the metallic central member. The ridges or grooves can act to grip the polymer of the outer portion during impaction of the device. The ridges or grooves can be aligned along a direction transverse to a longitudinal axis of the device, thereby the optimally withstand the forces associated with impaction of the device.

A connector can be provided at a proximal end of the device for attachment to a handle. The connector can be formed from a proximal end of the metallic central member, allowing for a robust connection to the handle. The connector can be a male or a female connector.

Alternatively, a proximal end of the device can form handle to be held by a surgeon during the procedure. In some embodiments, the metallic central member can extend into the handle, providing the device with additional strength.

A distal end of the metallic central member can extend through the outer portion to form a tip of the device. In this way, a relatively strong tip can be provided for chipping bone away.

The metallic central member can comprise a metallic plate. Such a plate, which may include features such as the engagement portion noted above, is easy to manufacture from sheet metal by a stamping process.

The metallic central member can, for example, comprise stainless steel, titanium or aluminium.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Embodiments of this invention can provide a device such as a broach or rasp for use in orthopaedic surgery. In particular, the device is intended for use in removing bone during orthopaedic surgery. The specific example illustrated in FIGS. 1 and 2 and described in detail below takes the form of a broach to be used for removing bone from the exposed section of a femoral neck following the cutting away of the femoral head at the neck, thereby to gain access to the medullary canal of the femur. The broach is also intended for use in removing bone from the medullary canal itself, in order to prepare the femur for the installation of an appropriately sized femoral implant. It will be appreciated, however, that a device such as a broach or a rasp according to an embodiment of this invention may be used in alternative surgical procedures for removing bone in other parts of the body.

As described in more detail below, the device includes a combination of metal and polymer parts. A metallic central member of the device provides the device with structural strength and rigidity, while the outer portion of the device, which comprises a polymer that can be moulded around the metallic central member, allows the cutting or rasping features of the device (for example teeth, ribs or ridges) to be formed in a manner that does not add significant weight. Overall, devices according to embodiments of this invention can retain a degree of rigidity that approximates the rigidity and sturdiness of earlier solid metal broaches or rasps while also enabling low cost and reduced weight. Accordingly, a device of the kind described herein may also be a single-use device that can be discarded after a surgical procedure, thereby avoiding the need to clean and sterilise the device for subsequent further use.

Figure 1:
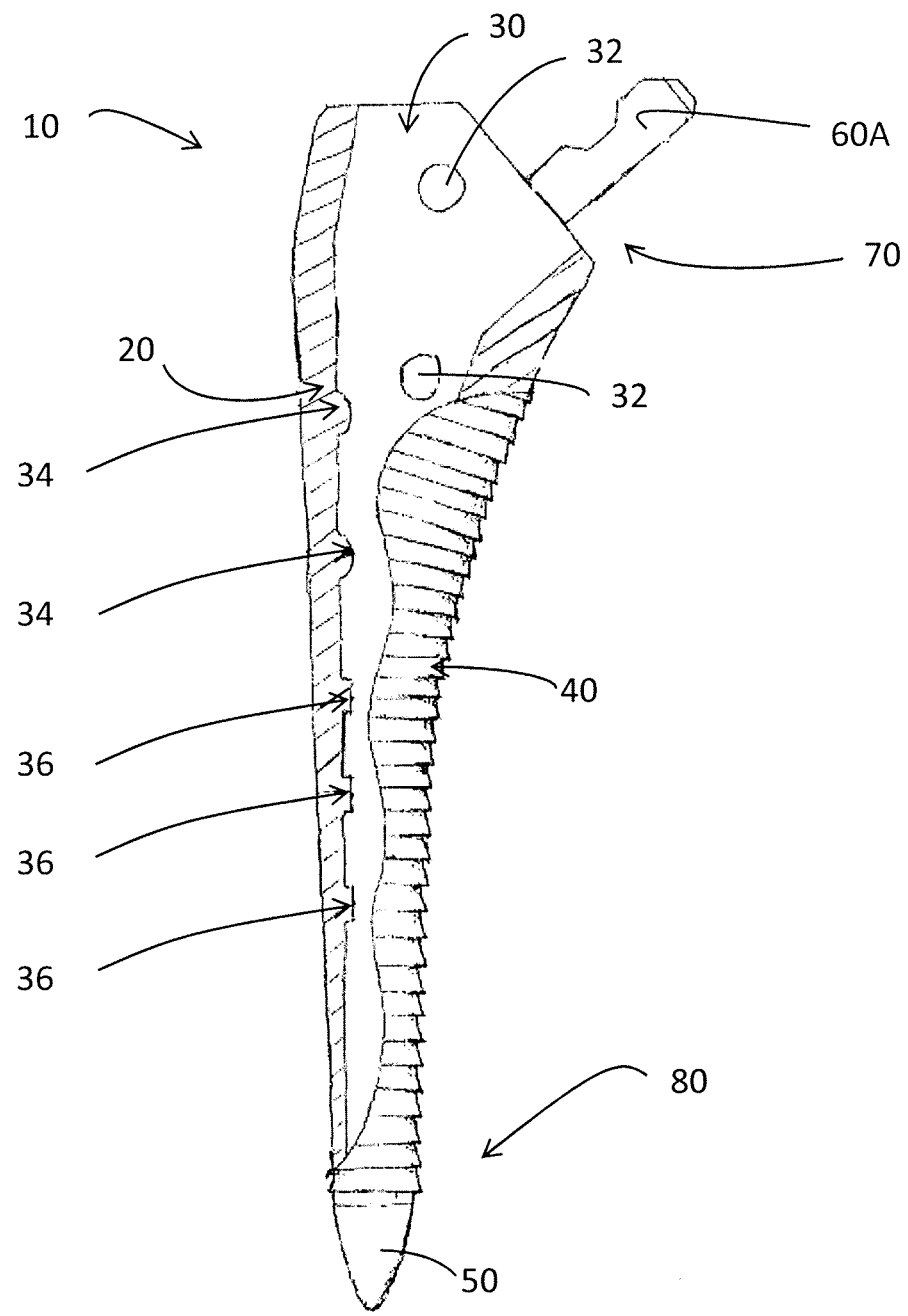
FIG. 1 shows a broach in accordance with an embodiment of the invention.

A first example of a device for use in orthopaedic surgery is shown in FIG. 1. The device 10 in FIG. 1 is a broach. As noted above, the broach can be used to remove bone from the medullary canal of a femur to prepare it for the installation of a femoral implant. The outer shape and dimensions of the broach can, as is known in the art, be chosen substantially to match the shape and configuration of the stem of the femoral implant that is to be inserted into the medullary canal. As described in more detail below, it is envisaged that a surgical kit can include a plurality of differently sized broaches of the kind shown in FIG. 1.

The device 10 includes an elongate body having a proximal end 70 and a distal end 80. The elongate body is comprised of two main structural parts, namely a metallic central member 30 and an outer portion 20. The outer portion 20 at least partially surrounds the metallic central member 30 and comprises a polymer. FIG. 1 shows a partial cut-away view of the device 10 so that the metallic central member 30 can be seen.

The metallic central member 30 provides structural strength and rigidity for the device 10. The outer portion 20 comprising a polymer includes features such as a profiled outer surface 40 (having teeth, ribs or ridges) for removing bone. The outer portion 20 can be appropriately shaped according to the size and configuration of the femoral implant as noted above.

The metallic central member 30 extends between the proximal end 70 and the distal end of the device 10. While the outer portion 20 at least partially surrounds the metallic central member 30, a part of the metallic central member 30 may be exposed at one or both ends of the elongate body. For example, in the present embodiment it is shown that a tip 50 of the broach 10 is formed from a distal end of the metallic central portion 30. The tip 50 can extend through the outer portion 20 to be exposed at the distal end 80 of the elongate body of the device 10. Because the tip of the device 10 is likely to experience significant structural stress during use, the provision of a metallic tip 50 of the kind shown in FIG. 1 advantageously provides additional strength for the part of the device 10 that is likely to require it most. Additionally, the provision of a tip 50 that is itself part of the metallic central member 30 allows the forces exerted on the tip 50 to be transferred back through the device to provide tactile feedback to the surgeon.

In use, the tip 50 can protect a leading edge of the profiled outer surface 40 of the outer portion 20 during impaction into bone, further improving the durability of the device 10. The tip 50 can, for example, be conical, rounded or bullet nosed. In some examples, an upper portion of the tip may overhang the leading edge.

At the proximal end 70 of the device 10, a connector 60A can be provided. The connector 60A in this example is formed from a proximal end of the metallic central member 30. The connector 60A provides a connection for attachment of the device 10 to a handle (not shown in the figures) to allow the surgeon to hold and manipulate the device 10 during a surgical procedure. It is noted that the provision of a metallic connector 60A as shown in FIG. 1 can advantageously provide a robust and structurally secure connection for attachment to the handle, since the connector 60A comprises metal and is not, for example, part of the outer portion comprising a polymer.

Figure 2:
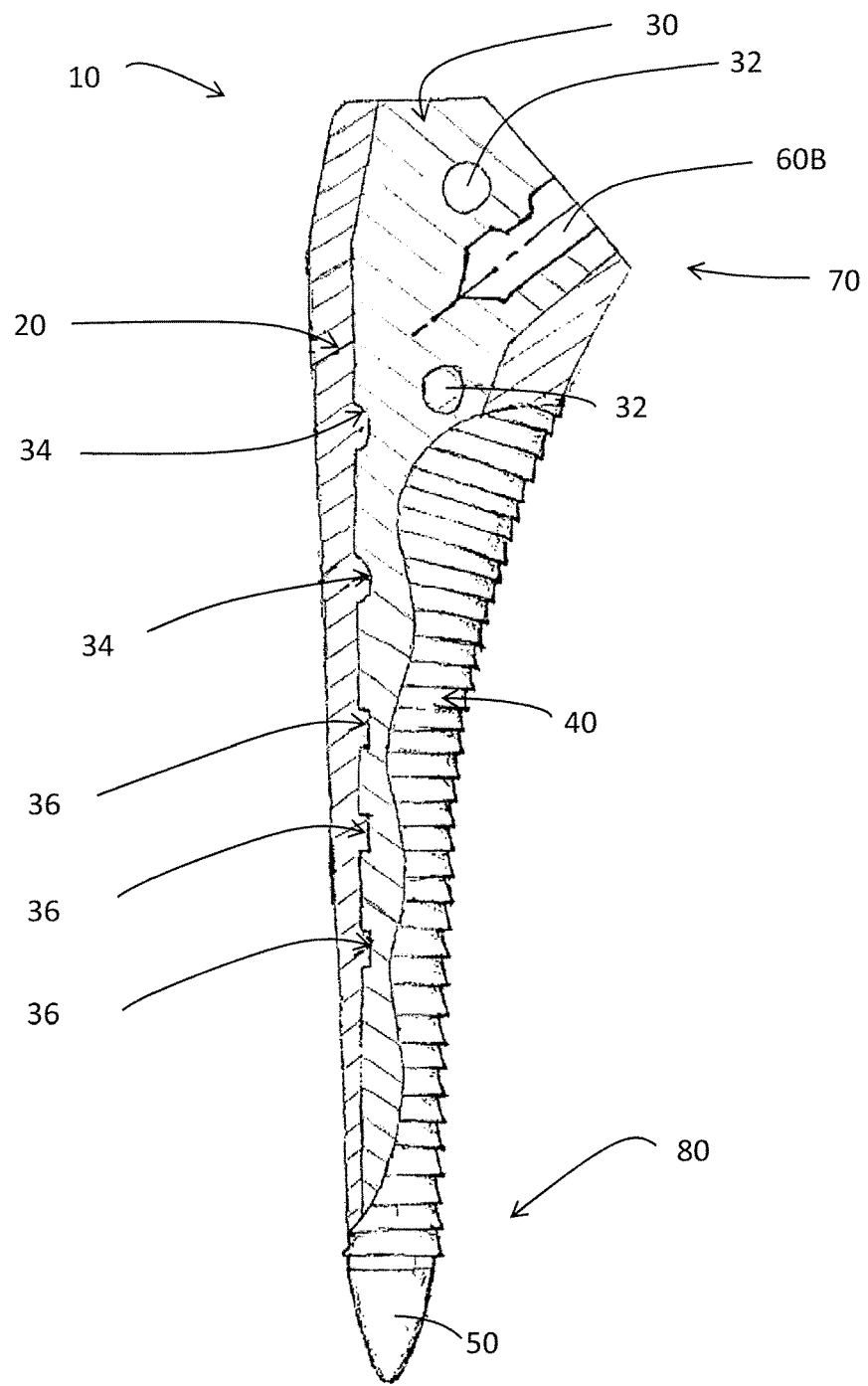
FIG. 2 shows a broach in accordance with another embodiment of the invention.

In the example of FIG. 1, the connector 60A is a male connector which can be engaged with a corresponding female connector of the handle. It is also envisaged that the connector at the proximal end 70 of the device may be a female connector. An example of a device 10 including a female connector 60B is illustrated in FIG. 2. The features of the device 10 in FIG. 2 are otherwise the same as those of the device 10 shown in FIG. 1. In FIG. 2, the connector 60B is configured to receive a corresponding a male connector of a handle. In common with the male connector 60A shown in FIG. 1, the female connector 60B shown in FIG. 2 is formed from the proximal end of the metallic central member 30. In particular, an opening in the proximal end of the metallic central member 30 can be provided. Since the opening is formed from metal, the structural strength and robustness of the connector 60B is likewise enhanced.

In some examples, instead of the provision of a connector 60A or 60B, it is envisaged that a proximal end 70 of the elongate body of the device 10 can form an integral handle. In this way, a separate handle and connector 60A or 60B need not be provided. In such examples, it is further envisaged that the metallic central member 30 can extend into the handle, thereby further increasing the structural strength of the overall device. The outer portion 20 can form an outer surface of the handle and can be appropriately shaped to be held in the surgeon's hands.

The metallic central member 30 can include one or more engagement features for resisting movement of the metallic central member relative to the outer portion 20 during use of the device 10 and for transferring the load on the profiled surface 40 to the metallic central member 30. These engagement features can take a number of forms.

In a first example, one or more apertures 32 can be provided, which pass through the metallic central member 30. The apertures 32 can be filled with the polymer of the outer portion 20.

In another example, the engagement features can comprise grooves 34, 36, which can be provided on an outer surface of the metallic central member 30. These grooves can also receive polymer of the outer portion 20. As shown in FIG. 1, the grooves can have a number of different configurations. The grooves 34 in FIG. 1 have a curved (for example, semi-circular) profile, while the grooves 36 have a rectangular or square profile. It is also envisaged that instead of (or as well as) having engagement features comprising grooves, the metallic central member 30 can include ribs which extend into the polymer of the outer portion 20. In common with the grooves 34, 36, the ribs can have a selected profile such as the curved or rectangular profiles noted above.

Each of the engagement features described above can increase the structural strength of the device 10 by resisting movement (for example rotational movement) of the metallic central member 30 relative to the outer portion 20 comprising a polymer during impaction of the device 10 for the removal of bone. In some examples, the orientation of the grooves or ridges can itself be chosen optimally to resist the impact forces associated with use of the device 10. For example, it is envisaged that the grooves or ridges 34, 36 can be aligned along a direction transverse to a longitudinal axis of the elongate body of the device 10.

The metallic central member 30 can comprise, for example, a metal plate. The plate can be stamped from sheet metal during manufacture. In other examples, the central metallic member 30 may comprise a metallic rod. The plate or rod can be provided with the engagement features described above using an appropriate conventional stamping or machining process. The cross sectional shape of the metallic central member 30 can be substantially flat (e.g. in the case that the metallic central member 30 is formed from a metal plate) or can approximate a circle or a quadrilateral (e.g. in the case that the metallic central member 30 is formed from a rod).

The features of the connector 60A, 60B and the tip 50 can be formed integrally with the metallic central member 30. For example, these features and a central part of the metallic central member that extends between them can be formed from a single piece. In alternative examples, the features of the tip 50 and/or the connector 60 can be added (attached) to the central portion of the metallic central member 30 (e.g. by welding) after the central portion has itself been produced.

The metallic central member 30 can comprise stainless steel, such as a surgical grade stainless steel of the kind that is known in the art. In other examples, titanium or aluminium can be used.

As noted above, the outer portion 20 surrounds the metallic central member 30 and has a profiled outer surface 40. The profiled outer surface 40 can include teeth, ribs and/or ridges that can be scraped against the bone to be removed. The configuration of the teeth, ribs and/or ridges is can be conventional and will not be elaborated upon further herein. The outer portion 20 can be formed using a conventional moulding process (e.g. injection moulding) to shape the polymer around a previously prepared metallic central member 30. The mould can be used to define the shape, size and configuration of the device 10 including the configuration of the profiled surface 40. The polymer can be an injection mouldable polymer and can be provided in some examples with other constituents such as fibres for reinforcement. The polymer can, for example, be IXEF (Polyarylamide), PAEK (Polyaryletherketone) or PEEK (Polyetheretherketone). The polymer may be chosen according to factors such as hardness and/or ability to withstand temperatures associated with autoclave sterilisation. For instance, the melting points of IXEF and PEEK are around 280° C. and 343° C., respectively, while PAEK has an operating temperature of around 250-350° C., while typical temperatures used in autoclave sterilisation may be around 120-140° C.

During a surgical procedure, the surgeon can select an appropriately sized broach to be used in accordance with the dimensions of the femoral implant. Also, as is known in the art, a surgeon may begin a bone removal procedure using a relatively small broach or rasp and subsequently use one or more larger devices of a similar kind as the opening in medullary canal is increased in size. Accordingly, a surgical instrument kit according to an embodiment of this invention can include a plurality of differently-sized devices of the kind described herein.

Accordingly, there has been described a device for use in orthopaedic surgery. The device includes a metallic central member. The device also includes an outer portion comprising a polymer. The outer portion surrounds the metallic central member. The outer portion has a profiled outer surface for removing bone. A surgical instrument kit is also described, the kit including a plurality of differently sized devices of the kind described herein. The device can be a broach or rasp. A method of removing bone during orthopaedic surgery has also been described.

Although particular embodiments of the invention have been described, it will be appreciated that many modifications/additions and/or substitutions may be made within the scope of the claimed invention.

The invention claimed is:

1. A device for use in orthopaedic surgery, the device comprising:

a metallic central member; and an outer portion comprising a polymer, wherein the outer portion surrounds the metallic central member and has a profiled outer surface for removing bone;

wherein the metallic central member comprises one or more engagement features for resisting movement of the metallic central member relative to the outer portion during impaction of the device and wherein at least one of the engagement features comprises an aperture passing through the metallic central member.

2. The device of claim 1, wherein a distal end of the metallic central member extends through the outer portion to form a tip of the device.

3. The device of any of claim 1 having a proximal end forming handle, wherein the metallic central member extends into the handle.

4. The device of claim 1, wherein the metallic central member comprises stainless steel, titanium or aluminium.

5. The device of claim 1 comprising a broach or rasp.

6. A surgical instrument kit, comprising:

a plurality of devices for use in orthopaedic surgery, each of the plurality of devices including a metallic central member, and an outer portion having a polymer, wherein the outer portion surrounds the metallic central member and has a profiled outer surface for removing bone, wherein at least one of the plurality of devices differs in size from at least one of the other of the plurality of devices.

7. A device for use in orthopaedic surgery, the device comprising:

a metallic central member; and an outer portion comprising a polymer, wherein the outer portion surrounds the metallic central member and has a profiled outer surface for removing bone:

wherein the metallic central member comprises one or more engagement features for resisting movement of the metallic central member relative to the outer portion during impaction of the device and wherein at least one of the engagement features comprises a ridge or a groove on an outer surface of the metallic central member.

8. The device of claim 7, wherein the ridges or grooves are aligned along a direction transverse to a longitudinal axis of the device.

9. A device for use in orthopaedic surgery, the device comprising:

a metallic central member; and an outer portion comprising a polymer, wherein the outer portion surrounds the metallic central member and has a profiled outer surface for removing bone:

wherein the device has a connector at a proximal end thereof for attachment to a handle and a proximal end of the metallic central member forms the connector.

10. A device for use in orthopaedic surgery, the device comprising:

a metallic central member; and an outer portion comprising a polymer, wherein the outer portion surrounds the metallic central member and has a profiled outer surface for removing bone:

wherein the metallic central member comprises a metallic plate.

* * * * *